Figure 4A:
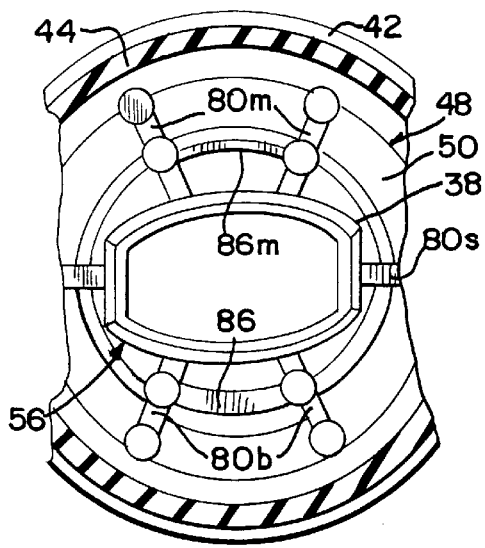

United States Patent [19]
Foley et al.

[11] Patent Number: 5,848,588
[45] Date of Patent: Dec. 15, 1998

[54] BACKPIECE FOR RECEIVING AN MDI ADAPTER IN AN AEROSOLIZATION SPACER

[75] Inventors: Martin P. Foley; Robert Morton, both of London, Canada

[73] Assignee: Trudell Medical Group, Canada

[21] Appl. No.: 734,388

[22] Filed: Oct. 17, 1996

Related U.S. Application Data

[63] Continuation of Ser. No. 248,716, May 25, 1994, abandoned.

[51] Int. Cl.$^6$ .................................................. A61M 11/00
[52] U.S. Cl. ............................ 128/200.23; 128/200.22; 128/200.14
[58] Field of Search .................... 128/200.14, 200.22, 128/200.23

[56] References Cited

U.S. PATENT DOCUMENTS

| | | | |
|---|---|---|---|
| 4,291,688 | 9/1981 | Kistler | 128/200.23 |
| 4,484,577 | 11/1984 | Sackner et al. | 128/200.23 |
| 4,706,663 | 11/1987 | Makiej | 128/200.23 |
| 5,012,803 | 5/1991 | Foley et al. | 128/200.23 |
| 5,012,804 | 5/1991 | Foley et al. | 128/200.23 |
| 5,040,527 | 8/1991 | Larson et al. | 128/200.23 |
| 5,042,467 | 8/1991 | Foley | 128/200.23 |
| 5,074,294 | 12/1991 | Chiesi | 128/200.23 |
| 5,203,323 | 4/1993 | Tritle | 128/200.23 |
| 5,385,140 | 1/1995 | Smith | 128/200.23 |
| 5,427,089 | 6/1995 | Kraemer | 128/200.23 |
| 5,477,849 | 12/1995 | Fry | 128/200.14 |
| 5,497,765 | 3/1996 | Praud et al. | 128/200.23 |
| 5,513,626 | 5/1996 | Hamilton | 128/200.23 |

OTHER PUBLICATIONS

Declaration of Martin P. Foley.

*Primary Examiner*—Aaron J. Lewis
*Attorney, Agent, or Firm*—Brinks Hofer Gilson & Lione

[57] ABSTRACT

A fitting is provided for mounting a metered dose inhaler and adapter on the entering upstream end of a cylindrical aerosolization spacer. The fitting includes a cylindrical portion mounting on the cylindrical wall of said aerosolization spacer, and further includes a transverse wall having therein a centrally disposed opening having an oval shape truncated at the ends. The opening is reinforced by radially disposed ribs having inner longitudinal edges, which with the edge of the truncated oval opening comprises the sole structure of the fitting engages the mouthpiece of a metered dose inhaler adapter. A non-leaking fit between the adapter and the fitting is produced notwithstanding the shape of a particular metered dose inhaler adapter mouthpiece, such as truncated oval, oval, or circular.

33 Claims, 3 Drawing Sheets

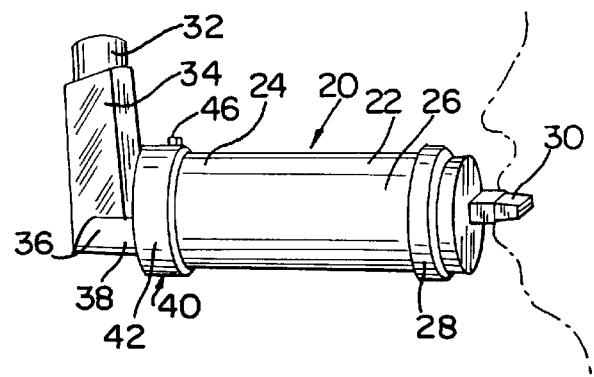

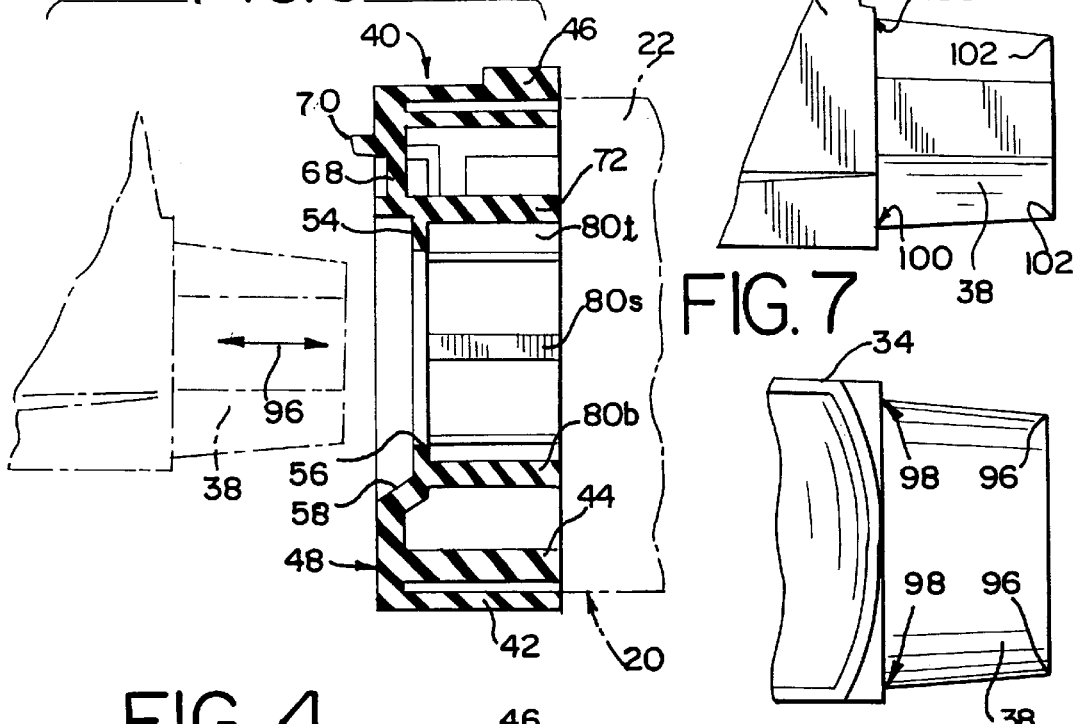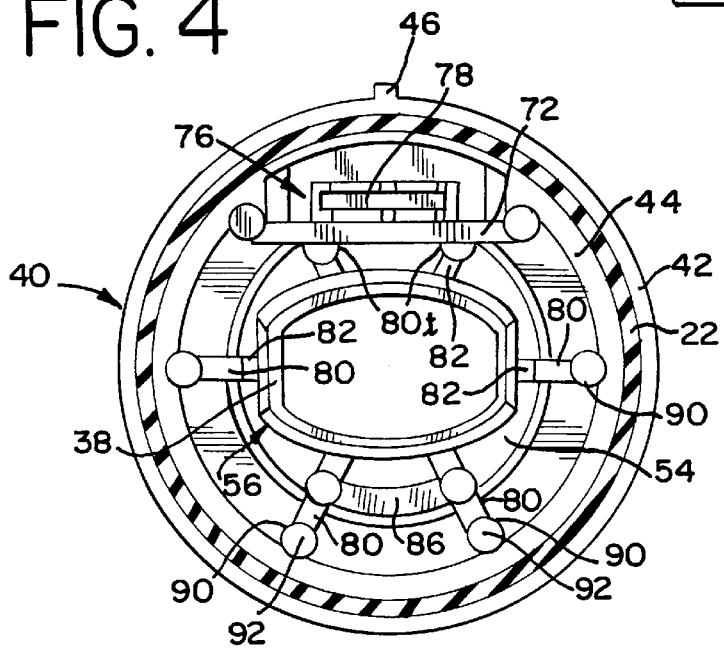

BACKPIECE FOR RECEIVING AN MDI ADAPTER IN AN AEROSOLIZATION SPACER

This application is a continuation of application Ser. No. 08/248,716, filed May 25, 1994 now abandoned.

BACKGROUND OF THE INVENTION

Asthmatic medications are commonly supplied in metered dose inhalers (generally referred to as MDIs) which are generally cylindrical canisters with axially extending vent tubes from internal valves. When the external tube or stem of a MDI canister is depressed it operates the internal valve to dispense a measured dose of medication from the stem. The medication is commonly packed in the canister with a suitable compressed gas to propel the medication and gas from the stem or tube when the latter is depressed. The manufacturer or distributor of the MDI canister generally supplies it with a substantially L-shaped adapter which receives the canister in substantially upright position, and has a substantial horizontal outlet portion for reception in the mouth of an asthmatic patient for inhalation of the medication. The propellent gas is stored as a liquid under pressure within the canister, and gasifies upon operation of the valve to expel the medication. Some of the gas is still in liquid condition when expelled with the medication, and drops of propellent and medication exit from the canister in various sizes. Drops of appropriate size are readily inhaled into the airway for action on the bronchi and lungs. However, larger drops are deposited in the mouth, and are swallowed, and therefore are ineffective as antiasthmatic medication.

It has been found that a simple expansion chamber, conveniently in the form of a small cylinder, promotes breaking down of the medication into smaller particles for efficient inhalation and action in the airways of the patient, while particles that remain too large are simply deposited in the cylinder. Such devices space the MDI adapter from the patient's mouth, and are often known as spacers. One such spacer that has found wide public acceptance and popularity is disclosed in Nowacki et al U.S. Pat. No. 4,470,412.

The spacer cylinder is generally provided at the upstream or entering end with a flexible, resilient adapter made of rubber or the like material. A central aperture is provided for receipt of the horizontal outlet portion of the MDI adapter. The horizontal outlet portions of MDI adapters differ among varying manufacturers. Some such horizontal portions have cross sections that are oval in shape, and some have such cross sections that are generally oval shaped but with vertical end walls. Still others use a circular cross section. This provides problems in the provision of a substantially universal inlet adapter for fitting for a spacer that will accept all, or substantially all, MDI adapter horizontal portions.

OBJECTS AND SUMMARY OF THE PRESENT INVENTION

It is an object of the present invention to provide an inlet adapter fitting for a cylindrical spacer which will efficiently receive all, or substantially all, known MDI adapters, regardless of the size and shape of such adapters.

In attaining this object we have provided a fitting of resilient, flexible material such as a rubber or the like. Concentric cylinders are provided which cover and grip the entering end of a cylindrical spacer. A transverse membrane extends inwardly from these concentric cylinders and is provided with a central opening for receipt of the MDI adapter. The hole is of essentially oval shape, but with straight end portions. Six ribs are formed integrally with the downstream side of the membrane, and are also directly radially inwardly from the innermost concentric cylinder, either directly or indirectly, and particular pairs of such ribs are provided with crossbracing, thereby controlling stretching of the diaphragm so that it provides a proper seal with an inserted MDI adapter. The radially inner ends of the ribs provide support for the MDI adapter.

THE DRAWINGS

The invention will best be understood from the following description when taken in connection with the accompanying drawings wherein:

FIG. 1 is a side, perspective view showing the spacer as used with an MDI adapter and canister;

FIG. 2 is a side view on an enlarged scale;

FIG. 3 is an enlarged perspective view of the fitting from the downstream end thereof;

FIG. 4 is a vertical sectional view on an enlarged scale taken substantially along the line 4—4 in FIG. 2;

FIG. 4*a* is a fragmentary view similar to a portion of FIG. 4, and showing a modification of the invention;

FIG. 5 is a vertical sectional view taken substantially along the line 5—5 in FIG. 3;

FIG. 6 is a fragmentary side view of the MDI adapter;

FIG. 7 is a fragmentary horizontal view of the same portion of the MDI adapter;

FIG. 8 is a view similar to FIG. 4, but shown with a larger MDI adapter;

FIG. 9 is a view similar to FIG. 4, but with an oval MDI adapter; and

FIG. 10 is a view similar to FIG. 8 with a circular MDI adapter.

DETAILED DISCLOSURE OF THE ILLUSTRATED EMBODIMENTS

A spacer 20 comprising an elongated cylindrical body 22 is shown in FIGS. 1 and 2. The body 22 is approximately 4.25" long and 1.75" in diameter, and is made of a suitable resinous plastic material. The body is open at both ends, and includes an upstream or entering end 24 shown at the left in the drawings, and a downstream or exit end 26 at the right. A fitting 28 including a mouthpiece 30 is assembled with the downstream or exit end. Alternatively, this fitting could include a mask rather than the mouthpiece. The spacer 20 is provided with internal valving to permit passage of air and medication upon inhalation from the upstream end 24 to the downstream 26, and on into the mouthpiece 30 and into a patient's bronchi and lungs. The valving is adjacent the downstream end, and prevents exhalation through the mouthpiece and fitting into the body 22, and preferably vents in an exhalation into the mouthpiece to outside air. Details on the valving structure and other portions of the fitting may be found in the aforesaid Nowacki et al U.S. Pat. No. 4,470,412.

Adjacent the upstream or entering end of the spacer there is a metered dose inhaler cartridge 32 of cylindrical construction, and having at its lower end an axially extending valve which will discharge a metered dose of liquid medication and gaseous propellent. The MDI canister or cassette 32 is housed in a substantially L-shaped adapter 34, having at its lower end an elbow 36 with a discharge end 38 extending to the right in the drawings. The adapter has been referred to as right angled, but preferably is of a slight obtuse angle greater than 90°. The exit portion 38 of the MDI adapter is received in a resilient fitting shown in some detail in FIGS. 2 and 3, and in subsequent figures to be referred to hereinafter. Such fitting is sometimes known colloquially as a backpiece or an MDI adapter.

The fitting or backpiece is preferably made of a soft rubber like material. A preferred example is a thermoplastic elastomer KRATON, a thermoplastic elastomer sold by Shell Oil Company and comprising a copolymer of styrene and butadien. The fitting or backpiece 40 is integrally molded as a single piece. It includes a pair of concentric rings, or flanges, specifically an outer ring 42 and an inner ring 44. The rings are spaced radially from one another, and are concentric, whereby to grip the upstream end of the cylinder 22 resiliently. The inner ring is thicker than the outer ring in order not to collapse inwardly away from the cylindrical housing, and the spacing between the rings is somewhat tapered to facilitate installation on the cylinder 22, and also to facilitate removal from a mold. A rib 46 extends upwardly from the downstream edge of the outer ring 42 in a radial direction. This rib is provided to orient the fitting 40 so that the rib 46 stands upwardly relative to the preferred position of the spacer 20 as shown in FIGS. 1 and 2.

The two cylindrical rings at 42 and 44 are concentric about a common axis of rotation. A transverse upstream wall 48 includes an annular ring 50 integrally joined to the upstream edges of the rings 42 and 44 to hold them in spaced relation. The wall ring 50 extends radially inwardly beyond the inner cylindrical ring 44 and at its inner edge has a rearwardly (downstream) frustoconical portion 52 continuing radially inwardly as a planar thin membrane 54.

The membrane 54 is thinner than the frustoconical indentation 52, and this is turn is thinner than the planar ring 50, the relative thicknesses being best seen in FIG. 5. The membrane 54 is provided with a central opening 56. This opening is relatively oval in shape, having curved upper 58 and lower 60 margins, and straight, parallel side margins 62 and 64. The oval opening 56 has a major axis extending between the two straight sides 62 and 64, and perpendicular to both. A minor axis extends vertically between the curved upper 58 and lower edges 60. The entire inner edge of the opening 56, comprising the edges 58, 60, 62 and 64 is not reinforced and it readily flexible and stretchable in and of itself. Note that the opening 56 is symmetric about the axis of rotation of the fitting 40.

In the preferred form of the invention (as shown in FIGS. 1–3 and 5, for example) the upper portion of the planar ring 50 is provided with a horizontal opening 66 with spaced vertical reinforcing bars 68 at the rear portion thereof. A horizontal shelf 70 protrudes forwardly from the planar ring 50 immediately above the top edge of the opening 66. The shelf 70 protrudes only a short distance upstream from the front surface of the ring 50.

A horizontal wall or shelf 72 extends downstream from the inner surface of the planar ring 50 and comprises a chord perpendicular to a radius of the ring 44. The top surface of the shelf 72, the downstream surface of the planar ring 50, the inner surface of the ring 44, and two vertical walls 74 extending between the chordal shelf 72 and the inner surface of the ring 44 cooperate to form a cavity 76. An audible sounding structure including a vibratory read 78 (FIG. 4 et seq) is housed in the cavity 76. This restructure is shown in detail in Foley U.S. Pat. No. 5,042,467, to which reference may be made for further details.

Six radially disposed ribs 80 are equally arcuately spaced about the back of the wall 48. The ribs are spaced at 60° arcs from one another and extend downstream from the wall 48, including the ring 50, the frustoconical inset 62, the membrane 54. Two of the ribs 80s lie in a horizontal plane and extend radially inwardly from the ring 44, having terminal edges 82 which are axial extensions from the vertical edges 62 and 64 of the opening 56. Two additional ribs 80b extend upwardly from a lower portion of the ring 44 and have their upper edges 84 coincident with the curved bottom edge 60 of the opening 56. The ribs 80b are interconnected by an arcuate spacing member 86 which interfits cylindrical member about the axis of rotation of the fitting 40. Two additional ribs 80t extend radially inwardly from the chordal wall or shelf 72, having inner surfaces 88 terminating at the top curved edge of the opening 56. As will be apparent, pairs of ribs lying on opposite sides of the opening 56 align with one another. All of the ribs run axially from the upstream wall 44 in a downstream direction to the downstream edge of the ring 44.

It will be noted that after each rib 80 is joined to the ring 44 by a cylindrical portion 90 having an exposed circular end 92. The cylindrical portions enforce the connection of the rib to the ring, and also help in controlling flexing or bending of each rib. Similarly, cylindrical sections 94 connect the crossbrace 86 to the bottom ribs 80b. The latter cylindrical sections also have circular ends 92. Besides it being simply the ends of the cylindrical sections, the circular ends represent impressions from a knockout punch to remove the thick fitting 40 from a mold.

Reference to FIGS. 4–7 discloses the interfitting of one conventional MDI adapter 34 with the fitting 40. The horizontal or mouthpiece portion 30 of the MDI adapter 34 is tapered, and this taper is somewhat exaggerated as are tapers of the fitting 40. In the present example the end or cross section of the mouthpiece 38 is of the same shape as the opening 56. Thus, the mouthpiece 38 is easily inserted axially and subsequently removed from the opening 56, as indicated by the double headed arrow 96 in FIG. 5. Once the mouthpiece is inserted all of the way, the fit of the mouthpiece in the opening 56 is snug, but not tight. As will be seen in FIG. 2 where the MDI adapter is shown in phantom, the shelf 70 prevents blockage of the reed orifice 76 by the nearly vertical portion of the MDI adapter 34. Engagement of the mouthpiece only by the edges 82 of the ribs allows the mouthpiece of the MDI adapter to move in and out of the opening or orifice 56 with reasonable ease. As will be apparent, the normal way of holding the MDI adapter 34 and the spacer 20 is to place the hand around the elbow 36 of the MDI adapter so that the index finger might readily depress the MDI canister 32. This precludes possible accidental withdrawal of the MDI adapter from the fitting. The thin nature of the membrane 54 allows the material to stretch slightly around the opening 56 to form a tight seal with the mouthpiece of the MDI adapter, thereby avoiding any inward leakage of air into the spacer 20.

Up to this point the fitting 40 has been described with the chamber 76 for the reed 78 and associated structure. In some instances it is not necessary to supply the reed. In this case the fitting is manufactured without the chamber and the reed, as shown in the fragmentary view of FIG. 4A. Substantially everything is the same as in FIG. 4, and identical numbers are used for the same parts. The distinction resides in that the reed 78 and chamber 76 are entirely omitted. The two upper ribs, identified as 80m extend radially all the way out to the ring 44, and are braced by a wall or brace 86m identical with the brace 86 between the two lower ribs 80b. Other than that the structure of the fitting is the same, and the interfit with the mouthpiece 38 of the MDI adapter is the same.

Figure 8:
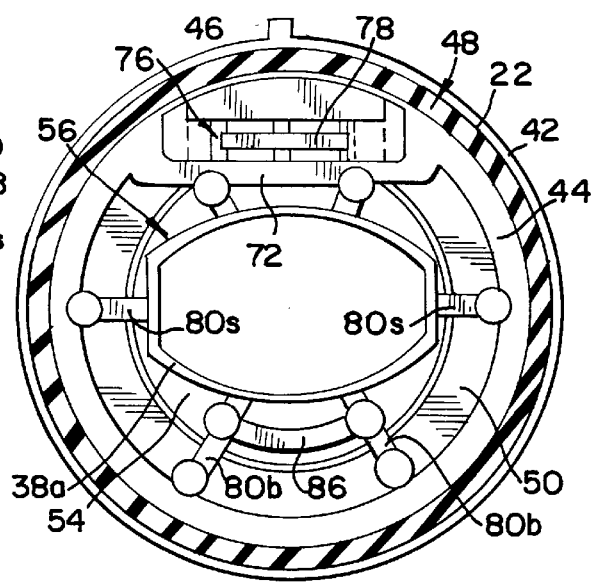

FIG. 8 is substantially identical with FIG. 4, except that the MDI adapter mouthpiece 38a is of larger transverse dimension. This causes all of the ribs to compress slightly, and it causes the membrane 54 to stretch around the opening 56 to accommodate the slightly larger mouthpiece.

Figure 9:
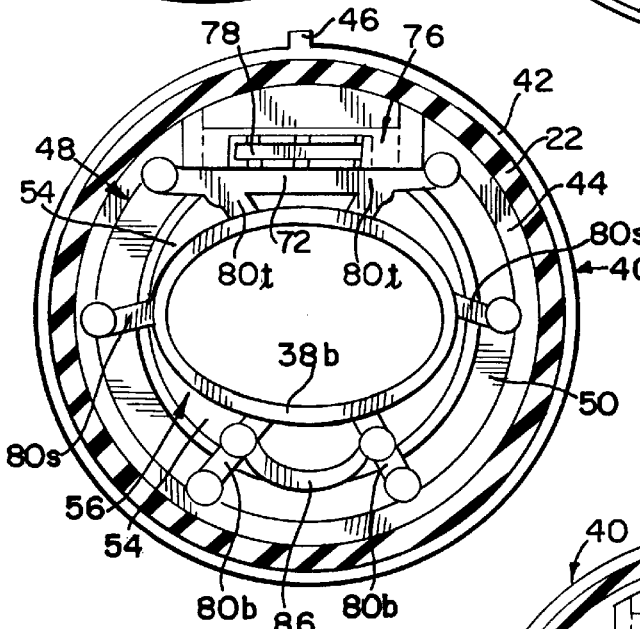

FIG. 9 is also very similar to FIG. 4. Indeed, the fitting 40 is identical. However, in this case the mouthpiece 38b of the MDI adapter is somewhat larger, and is completely oval in end view or cross section. However, this mouthpiece fits just as well, with the membrane 54 stretching further about the opening 56. In addition, the upper ribs 80t cannot move upwardly because the shelf or floor is held fixedly in place by the reed structure tightly filling the compartment 76. The ribs 80t thus compress to a considerable extent, and may somewhat deflect upwardly. The horizontal or center ribs 80s will deflect. The deflection may be up, as shown, or it may be down, or one may be up and the other down. The direction of deflection depends on how the user manipulates the MDI adapter in inserting the mouthpiece 38b. However, a big change will be noted at the bottom, where the ribs 80b deflect rather substantially toward one another, and the brace 86 is bent into a tighter curve than in FIG. 4.

FIG. 10 again is similar to FIG. 4, and the fitting 40 is identical. However, in this instance the MDI adapter mouthpiece 38c is circular. The area of the circular mouthpiece is about the same as that of the oval mouthpiece in FIG. 8, with the horizontal dimension thus being reduced, and the vertical dimension being increased. As before, the ribs 80t cannot move up because of the backing of the shelf 92 by the reed structure. The ribs can compress just so much, and the result is that the center or axis of rotation of the mouthpiece, indicated at 94 is shifted parallel to itself down from the axis of rotation 92 of the fitting 40. In prior examples the two centers have coincided. This again causes the side ribs 80 as to deflect, generally downwardly, but possibly upwardly, or one up and one down, depending upon the manner of handling of the MDI mouthpiece upon insertion. The lowermost ribs 80b deflect even farther than in FIG. 9, and the cross member or brace 86 folds into an even tighter bend, probably in most instances engaging the inner surface of the ring 44. However, due to the flexibility of the of the membrane 50, and the resiliency thereof, a tight seal is maintained between the membrane and the mouthpiece 38c.

As will now be seen the fitting as herein shown and described can adapt to various sizes and shapes of mouthpiece without any changes in dimension of the fitting as manufactured. Not withstanding such adaptation, there is no leakage between the fitting and the mouthpiece. Furthermore, the mouthpiece in each instance is engaged only by the ends or narrow portions of the ribs (as in FIG. 10) whereby insertion and withdrawal of the mouthpiece of the MDI adapter is greatly facilitated.

Certain dimensions of the MDI adapter mouthpiece relative to corresponding dimensions of the present fitting are important, as are dimensions of the fitting itself. As will be understood, it is the outside dimensions of the mouthpiece that are important, and turning first to the MDI adapter mouthpiece as shown in FIGS. 4–7, the dimension across the flat sides 38 (that is from one side to another) at the outer end of the mouthpiece at 96 is 0.883". At the inner end between the points 98 (see FIG. 7) the corresponding dimension is 1.03", the dimensions being taken from a typical specimen. The maximum dimension across the curved surfaces, between points 100 (FIG. 6) is 0.701". The same dimension at the outer end of the mouthpiece, as indicated between points 102 is 0.651". The length of the mouthpiece is 0.561". It is to be borne in mind that these particular dimensions have been taken from an actual production specimen, and that the design measurements may be slightly different, due to the difficulty of holding precise tolerances in molded plastic materials at a commercially acceptable cost. Comparison of the dimension with the drawing will confirm what has been noted heretofore that the taper in the drawings in each instance is somewhat amplified for illustrative purposes.

Turning to the oval mouthpiece shown in FIG. 9, the maximum or outside dimension of the major axis 1.00", providing an almost indecernable taper. Corresponding minor axis dimensions are 0.780" and 0.784". The length of this mouthpiece is 0.488".

Figure 10:
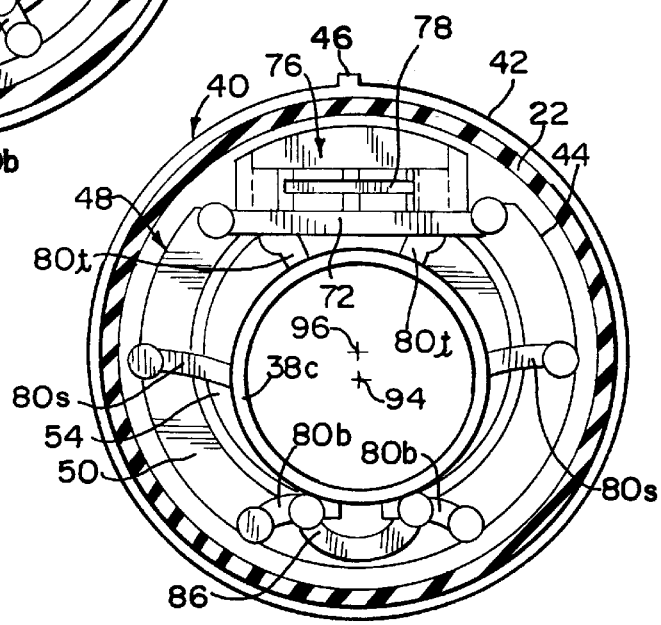

The circular mouthpiece of FIG. 10 has a non-tapering diameter of 0.964" and a length of 1.02".

Dimensions of the actual fitting 40 of the present invention are set forth hereinafter. The distance between the flat ends 62 and 64 of the opening 56 is 0.900". The radius of curvature of each of the curved edges 58 and 60 is 0.610", and the maximum dimension across the curved edges, i.e., the minor dimension of the oval is 0.684". The length of each straight edge 62, 64 is 0.300". The thickness of the membrane 54 in which the hole or opening 56 is located is 0.040".

The length of each rib 80 axially of the fitting is from the front face of the membrane 54 to the inner end of the reed 0.500". Each rib is approximately 0.080" thick.

It will thus be seen that the single opening or aperture 56 of the shape shown and described will accommodate mouthpieces of varying cross sectional shapes and dimensions without allowing leakage. Furthermore, engagement of the mouthpieces by the thin diaphragm 54 seals against leakage, but does not provide undue entrance and movement of mouthpieces thereinto. The mouthpieces primarily engage the ends of the ribs 80 which present minimum frictional resistance to entry of the mouthpieces due to the relatively narrow nature of the ribs. From that point, once the mouthpiece is fully inserted the ribs provide excellent stability to the mouthpiece.

The specific example of the invention as herein shown and described is for illustrative purposes only. Various changes in structure will no doubt occur to those skilled in the art, and will be understood as comprising a part of the present invention insofar as they fall within the spirit and scope of the appended claims.

The invention is claimed as follows:

1. A fitting for selectively mounting any of a plurality of metered dose inhaler adapters on an inlet end of a cylindrical aerosolization spacer, wherein said plurality of metered dose inhaler adapters have respectively different sizes or shapes of outlet mouthpieces, said fitting comprising a one-piece integral member molded of a resilient, flexible elastomeric material, said fitting comprising:

an outer cylindrical portion having a longitudinal extending axis of rotation for mounting said fitting on a cylindrical aerosolization spacer;

an integral transverse wall extending radially inwardly from said outer cylindrical portion, said integral transverse wall having a substantially central opening for receipt of an outlet mouthpiece of a metered dose inhaler adapter said central opening having a peripheral edge shaped substantially as a truncated oval having a major axis and having a pair of curved sides and a pair of opposite ends directed chordally of said oval and substantially perpendicular to the major axis of said oval; and a plurality of ribs in angularly spaced relation about said transverse wall and said cylindrical portion and integral with said wall and said cylindrical portion, said ribs extending from said transverse wall in a direction of said axis of rotation, each rib having an inner longitudinally extending edge substantially parallel to said axis of rotation for engaging and supporting the outlet mouthpiece of a metered dose inhaler adapter and for bracing and reinforcing said transverse wall, said edges of all of said ribs being of substantially equal length parallel to said axis of rotation, said ribs extending substantially radially outwardly from said longitudinally extending edges towards said cylindrical portion, there being no metered dose inhaler outlet mouthpiece engaging portion of said fitting extending radially inwardly of said rib edges whereby only said peripheral edge of said wall opening and said longitudinally extending rib edges are engageable with a metered dose inhaler adapter outlet mouthpiece.

2. A fitting as set forth in claim 1 wherein said plurality of said ribs includes a pair of ribs adjacent one of said curved sides of said opening, and a curved bracing wall between said pair of ribs and spaced radially outwardly of one of said curved sides.

3. A fitting as set forth in claim 2 and further including a second pair of ribs opposite to said first mentioned pair of ribs and respectively aligned with said mentioned pair.

4. A fitting as set forth in claim 1 and further including interiorly of said cylindrical portion and adjacent said transverse wall a compartment for a vibratory reed including a substantially chordal wall extending across said cylindrical portion and adjacent one of the curved walls of said opening and extending from said transverse wall substantially in the direction of said longitudinal axis of rotation, and a pair of said plurality of ribs extending outwardly from one of said curved sides only to and joined to said chordal wall.

5. A fitting as set forth in claim 2 and further including interiorly of said cylindrical portion and adjacent said transverse wall a compartment for a vibratory reed including a substantially chordal wall extending across said cylindrical portion and adjacent one of the curved walls of said opening and extending from said transverse wall substantially in the direction of said longitudinal axis of rotation, and a pair of said plurality of ribs extending outwardly from one of said curved sides only to and joined to said chordal wall.

6. A fitting as set forth in claim 5 and further including a reed structure disposed within said compartment and backing said chordal wall and thereby preventing displacement of said chordal wall, said chordal wall thereby limiting radial outward movement of the edges of the two walls joined to the chordal wall, a pair of ribs opposite to the pair of ribs joined to the chordal wall and being deflectable, and a bracing wall interconnecting the second mentioned pair of ribs and being flexible to allow deflection of said second pair of ribs.

7. A fitting as set forth in claim 1 wherein an radially outer portion of said transverse wall is of predetermined thickness, and an inner portion of said transverse wall in which said opening is disposed being of less thickness than said predetermined thickness to permit stretching of said opening and accommodation of a metered dose inhaler adapter outlet mouthpiece.

8. The combination comprising one of a plurality of metered dose inhalers including a cartridge and a metered dose inhaler adapter having an outlet mouthpiece, a cylindrical aerosolization spacer having a cylindrical inlet end, and a fitting mounted on said aerosolization spacer inlet end and receiving the outlet mouthpiece of said metered dose inhaler adapter, said fitting comprising a one-piece integral member molded of a resilient flexible elastomeric material and including an outer cylindrical portion having a longitudinally extending axis of rotation and being received on the inlet end of said aerosolization spacer, said fitting further including an integral transverse wall extending radially inwardly from said cylindrical portion and having a substantially central opening for receipt of the outlet mouthpiece of said metered dose inhaler adapter and having a peripheral edge shaped substantially as a truncated oval having a major axis and having a pair of curved sides and opposite ends directed chordally of said oval and substantially perpendicular to said major axis of said oval, and a plurality of ribs in angularly spaced relation about said transverse wall and said cylindrical portion and integral with said wall and with said cylindrical portion, said ribs extending from said wall in the direction of said axis of rotation, each rib having an inner longitudinally extending edge substantially parallel to said axis of rotation for engaging and supporting said outlet mouthpiece of said metered dose inhaler adapter and for bracing and reinforcing said transverse wall, said edges of all of said ribs being of substantially equal length parallel to said axis of rotation, said ribs extending substantially radially outwardly from said longitudinally extending edges toward said cylindrical portion, there being no portion of said fitting extending radially inwards of said rib edges, whereby only said peripheral edge of said wall opening and said longitudinally extending rib edges are engageable with said metered dose inhaler adapter outlet mouthpiece.

9. The combination as set forth in claim 8 wherein an transverse shape of said metered dose inhaler adapter outlet mouthpiece is a truncated oval complimentary to and interfitting with said opening.

10. The combination as set forth in claim 8 wherein an transverse shape of said metered dose inhaler outlet mouthpiece is that of a non-truncated oval and interfits with said opening.

11. The combination as set forth in claim 8 wherein the transverse shape of said metered dose inhaler outlet mouthpiece is circular and interfits with said opening.

12. In combination:
a metered dose inhaler canister;
a metered dose inhaler adapter for receiving the metered dose inhaler canister and dispensing an aerosol from the metered dose inhaler canister through a mouthpiece of the metered dose inhaler adapter; and
an aerosolization spacer having
an inlet connected to said mouthpiece of said metered dose inhaler adapter to receive the aerosol dispensed therefrom and
an outlet from which a patient can receive said aerosol,
wherein the improvement comprises:
a backpiece connected to the inlet of said aerosolization spacer, said backpiece comprising means for accommodating various sizes and shapes of metered dose inhaler adapter mouthpieces said accommodating means comprising a flexible, resilient opening means that flexibly conforms to different sizes of metered does inhaler mouthpieces.

13. The invention of claim 12 wherein said backpiece further comprises:
means for providing a tight seal around one of said metered dose inhaler mouthpieces.

14. The invention of claim 12 further comprising:

an audible sounding structure connected to said aerosolization spacer.

15. The invention of claim 14 wherein said audible sounding structure is connected to said backpiece.

16. The invention of claim 15 further comprising:
a shelf connected to said backpiece adjacent to said audible sounding structure.

17. The invention of claim 12 wherein said backpiece includes an oval opening into which said mouthpiece of said metered dose inhaler adapter is received, and further comprising:
a membrane surrounding said oval opening.

18. The invention of claim 17 wherein said membrane is relatively thinner than portions of said backpiece adjacent thereto.

19. The invention of claim 12 wherein said backpiece is composed of KRATON, a thermoplastic elastomer comprised of a copolymer of styrene and butadien.

20. The invention of claim 12 wherein said backpiece includes an oval opening into which said mouthpiece of said metered dose inhaler adapter is received, and wherein said accommodating means comprises:
a plurality of rib edges located interiorly of said oval opening.

21. The invention of claim 20 wherein said plurality of rib edges comprises six rib edges.

22. In combination:
an aerosolization spacer having a hollow spacer body having an inlet end and an outlet end from which a patient can receive an aerosol medication, wherein said aerosolization spacer is adapted for use with a metered dose inhaler adapter and a metered dose inhaler canister that dispenses an aerosol from a mouthpiece of the metered dose inhaler adapter,
wherein the improvement comprises:
a backpiece fitting connected to said inlet end of said spacer body, said backpiece fitting having an opening located therein for receiving the mouthpiece of said metered dose inhaler adapter, said backpiece fitting being formed of a separate piece of material and easily removable from said spacer body to enable cleaning thereof, and further wherein said backpiece fitting includes means to stretchably deflect to accommodate different sizes and shapes of mouthpieces on different inhaler adapters whereby a single backpiece can accommodate different sizes and shapes of metered dose inhaler adapters and metered dose inhaler canisters.

23. In combination:
an aerosolization spacer having a hollow spacer body formed of a plastic material and having an inlet end and an outlet end from which a patient can receive an aerosol medication, wherein said aerosolization spacer is adapted for use with a metered dose inhaler adapter and a metered dose inhaler canister that dispenses an aerosol from a mouthpiece of the metered dose inhaler adapter,
wherein the improvement comprises:
a backpiece fitting connected to said inlet end of said spacer body, said backpiece fitting having an opening located therein for receiving the mouthpiece of said metered dose inhaler adapter, said backpiece fitting being formed of a soft rubber-like, resilient material to enable said opening of said backpiece fitting to form an airtight seal about the mouthpiece of the metered dose inhaler.

24. In combination:
an aerosolization spacer having a hollow spacer body having an inlet end and an outlet end from which a patient can receive an aerosol medication, wherein said aerosolization spacer is adapted for use with a metered dose inhaler adapter and a metered dose inhaler canister that dispenses an aerosol from a mouthpiece of the metered dose inhaler adapter,
wherein the improvement comprises:
a backpiece fitting connected to said inlet end of said spacer body, said backpiece fitting having an opening located therein for receiving the mouthpiece of said metered dose inhaler adapter, said backpiece fitting being formed of a soft rubber-like, resilient material that is different than the material from which the spacer body is formed, wherein said resilient material of said backpiece fitting enables said opening thereof to stretchably deflect to accommodate different sizes and shapes of mouthpieces on different inhaler adapters whereby a single backpiece can accommodate different sizes and shapes of metered dose inhaler adapters and metered dose inhaler canisters.

25. In combination:
an aerosolization spacer having a hollow spacer body having an inlet end and an outlet end from which a patient can receive an aerosol medication, wherein said aerosolization spacer is adapted for use with a metered dose inhaler adapter and a metered dose inhaler canister that dispenses an aerosol from a mouthpiece of the metered dose inhaler adapter,
wherein the improvement comprises:
a backpiece fitting connected to said inlet end of said spacer body, said backpiece fitting having an opening located therein for receiving the mouthpiece of said metered dose inhaler adapter, said backpiece fitting being formed of a separate piece of material and easily removable from said spacer body to enable cleaning thereof, and further wherein said material is a soft rubber-like, resilient material to enable said opening of said backpiece fitting to stretchably deflect to accommodate different sizes and shapes of mouthpieces on different inhaler adapters and further comprising means for forming an airtight seal about the mouthpiece of the metered dose inhaler.

26. A fitting for selectively mounting a metered dose inhaler adapter on an inlet end of a cylindrical aerosolization spacer, wherein said metered dose inhaler adapter has an outlet mouthpiece and wherein said fitting comprises a one-piece integral member molded of a resilient, flexible elastomeric material, said fitting comprising:
an outer cylindrical portion having a longitudinal extending axis of rotation for mounting said fitting on a cylindrical aerosolization spacer;
an integral transverse wall extending radially inwardly from said outer cylindrical portion, said integral transverse wall having a substantially central opening for receipt of an outlet mouthpiece of a metered dose inhaler adapter, said central opening having a peripheral edge shaped substantially as a truncated oval having a major axis and having a pair of curved sides and a pair of opposite ends directed chordally of said oval and substantially perpendicular to the major axis of said oval;
a shelf protruding longitudinally from said integral transverse wall adjacent one of said pair of curved sides of said central opening;

a brace protruding longitudinally from said integral transverse wall adjacent the other of said pair of curved sides of said central opening; and a plurality of ribs in angularly spaced relation about said transverse wall and said cylindrical portion and integral with said wall and said cylindrical portion, said ribs extending longitudinally in a direction of said axis of rotation and radially inward from said shelf and said brace, each rib having an inner longitudinally extending edge substantially parallel to said axis of rotation.

27. The fitting of claim 26 wherein said ribs are spaced from each other by 60 degrees.

28. The fitting of claim 26 wherein said integral transverse wall includes an opening therethrough between said shelf and said outer cylindrical portion, said opening adapted to receive a sounding structure.

29. The fitting of claim 26 further comprising:

an inner ring outer spaced radially inward from said cylindrical portion and extending in a longitudinal direction from said integral transverse wall.

30. A fitting for mounting a metered dose inhaler adapter on an inlet end of a cylindrical aerosolization spacer, wherein said metered dose inhaler adapter has an outlet mouthpiece, said fitting comprising a one-piece integral member molded of a resilient, flexible elastomeric material, said fitting comprising:

an outer cylindrical portion having a longitudinal extending axis of rotation for mounting said fitting on the cylindrical aerosolization spacer;

an inner ring spaced radially inward from said outer cylindrical portion and extending in a longitudinal direction;

an integral transverse wall extending radially inwardly from said outer cylindrical portion and said inner ring, said integral transverse wall having a substantially central opening for receipt of an outlet mouthpiece of a metered dose inhaler adapter, said central opening having a peripheral edge shaped substantially as a truncated oval having a major axis and having a pair of curved sides and a pair of opposite ends directed chordally of said oval and substantially perpendicular to the major axis of said oval;

a shelf protruding longitudinally from said integral transverse wall adjacent one of said pair of curved sides of said central opening;

a brace protruding longitudinally from said integral transverse wall adjacent the other of said pair of curved sides of said central opening; and a first pair of ribs located on said shelf on a side thereof facing said central opening and extending longitudinally in a direction of said axis of rotation; and a second pair of ribs located on said brace on a side thereof facing said central opening and extending longitudinally in a direction of said axis of rotation.

31. The fitting of claim 29 wherein said integral transverse wall comprises;

an annular ring portion integrally joining upstream edges of said outer cylindrical ring and said inner ring; and a frustoconical portion continuing inwardly as a planar thin membrane to said central opening.

32. An aerosol delivery system for a metered dose inhaler adapter wherein said metered dose inhaler adapter has an outlet mouthpiece, said aerosol delivery system comprising:

a cylindrical aerosolization spacer having an inlet end and an outlet end; and a fitting mounted on said inlet end of said cylindrical aerosolization spacer, said fitting formed of a one-piece integral member molded of a resilient, flexible elastomeric material and comprising:

an outer cylindrical portion having a longitudinal extending axis of rotation;

an inner ring spaced radially inward from said outer cylindrical portion and extending in a longitudinal direction, wherein said outer cylindrical portion and said inner ring define a circular cavity into which said inlet end of said cylindrical aerosolization spacer is received;

an integral transverse wall extending radially inwardly from said outer cylindrical portion and joining upstream edges of said outer cylindrical portion and said inner ring, said integral transverse wall having a substantially central opening for receipt of the outlet mouthpiece of the metered dose inhaler adapter, said central opening having a peripheral edge shaped substantially as a truncated oval having a major axis and having a pair of curved sides and a pair of opposite ends directed chordally of said oval and substantially perpendicular to the major axis of said oval;

a shelf extending longitudinally from said integral transverse wall adjacent one of said pair of curved sides of said central opening;

a brace extending longitudinally from said integral transverse wall adjacent the other of said pair of curved sides of said central opening;

a first plurality of ribs located on said shelf on a side thereof facing said central opening and extending longitudinally in a direction of said axis of rotation, and a second plurality of ribs located on said brace on a side thereof facing said central opening and extending longitudinally in a direction of said axis of rotation.

33. The aerosol delivery system of claim 32 wherein each rib is approximately 0.080 inches thick.

* * * * *